US008363450B2

(12) United States Patent
Jung et al.

(10) Patent No.: US 8,363,450 B2
(45) Date of Patent: Jan. 29, 2013

(54) HIERARCHICAL CROSS-POINT ARRAY OF NON-VOLATILE MEMORY

(75) Inventors: Chulmin Jung, Eden Prairie, MN (US); Yong Lu, Edina, MN (US); Insik Jin, Eagan, MN (US); YoungPil Kim, Eden Prairie, MN (US); Harry Hongyue Liu, Maple Grove, MN (US)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 13/280,109

(22) Filed: Oct. 24, 2011

(65) Prior Publication Data

US 2012/0039112 A1 Feb. 16, 2012

Related U.S. Application Data

(63) Continuation of application No. 12/502,199, filed on Jul. 13, 2009, now Pat. No. 8,098,507.

(51) Int. Cl.
*G11C 11/00* (2006.01)
(52) U.S. Cl. .......................................... 365/148; 365/158
(58) Field of Classification Search .................. 365/148, 365/185.18, 230.03, 158
See application file for complete search history.

(56) References Cited

U.S. PATENT DOCUMENTS

| 5,625,780 A | 4/1997 | Hsieh et al. |
| 6,125,066 A | 9/2000 | Gratz et al. |
| 6,597,598 B1 * | 7/2003 | Tran et al. ........................ 365/94 |
| 6,686,624 B2 | 2/2004 | Hsu |
| 7,190,615 B2 | 3/2007 | Fujito et al. |
| 7,342,826 B2 | 3/2008 | Fujito et al. |
| 7,359,226 B2 | 4/2008 | Schwerin |
| 7,433,242 B2 | 10/2008 | Ohsawa |
| 7,460,388 B2 | 12/2008 | Ilda |
| 7,463,546 B2 | 12/2008 | Fasoli et al. |
| 7,471,579 B2 | 12/2008 | Uchikoba et al. |
| 7,505,347 B2 * | 3/2009 | Rinerson et al. .............. 365/209 |
| 2002/0006061 A1 | 1/2002 | Poechmueller |
| 2002/0034117 A1 | 3/2002 | Okazawa |
| 2010/0110765 A1 | 5/2010 | Tian et al. |

FOREIGN PATENT DOCUMENTS

| EP | 0104120 A2 | 3/1984 |
| EP | 1526548 A1 | 4/2005 |

* cited by examiner

*Primary Examiner* — Son Dinh
(74) *Attorney, Agent, or Firm* — Hall Estill Attorneys at Law (57) ABSTRACT

A method and apparatus for reading data from a non-volatile memory cell. In some embodiments, a cross-point array of non-volatile memory cells is arranged into rows and columns. A selection circuit is provided that is capable of activating the first block of memory cells while deactivating the second block of memory cells. Further, a read circuit is provided that is capable of reading a logical state of a predetermined memory cell in the first block of memory cells with a reduced leak current by programming a first resistive state to the block selection elements corresponding to the first block of memory cells while programming a second resistive state to the block selection elements corresponding to the second block of memory cells.

21 Claims, 7 Drawing Sheets

FIG. 10 ated in FIG. 1.

HIERARCHICAL CROSS-POINT ARRAY OF NON-VOLATILE MEMORY

RELATED APPLICATION

This application is a continuation of copending U.S. patent application Ser. No. 12/502,199 filed Jul. 13, 2009.

BACKGROUND

Data storage devices generally operate to store and retrieve data in a fast and efficient manner. Some storage devices utilize a semiconductor array of solid-state memory cells to store individual bits of data. Such memory cells can be volatile (e.g., DRAM, SRAM) or non-volatile (RRAM, STRAM, flash, etc.).

As will be appreciated, volatile memory cells generally retain data stored in memory only so long as operational power continues to be supplied to the device, while non-volatile memory cells generally retain data storage in memory even in the absence of the application of operational power. However, an array of non-volatile memory cells can generate an unwanted current during various operations. Such unwanted current can be problematic in quickly and consistently reading data from the array of memory cells.

As such, in these and other types of data storage devices it is often desirable to increase efficiency and reliability, particularly by improving the utilization of memory space by reducing overhead storage space associated with updating data.

SUMMARY

Various embodiments of the present invention are directed to a method and apparatus for reading data from a non-volatile memory cell.

In some embodiments, a cross-point array of non-volatile memory cells is arranged into rows and columns. A selection circuit is provided that is capable of activating the first block of memory cells while deactivating the second block of memory cells. Further, a read circuit is provided that is capable of reading a logical state of a predetermined memory cell in the first block of memory cells with a reduced leak current by programming a first resistive state to the block selection elements corresponding to the first block of memory cells while programming a second resistive state to the block selection elements corresponding to the second block of memory cells.

In other embodiments, a cross-point array of non-volatile memory cells arranged into rows and columns, a selection circuit capable of activating the first block of memory cells while deactivating the second block of memory cells, and a read circuit are provided. A logical state of a predetermined memory cell in the first block of memory cells is then read with a reduced leak current by programming a first resistive state to the block selection elements corresponding to the first block of memory cells while programming a second resistive state to the block selection elements corresponding to the second block of memory cells.

These and various other features and advantages which characterize the various embodiments of the present invention can be understood in view of the following detailed discussion and the accompanying drawings.

DETAILED DESCRIPTION

Figure 1:
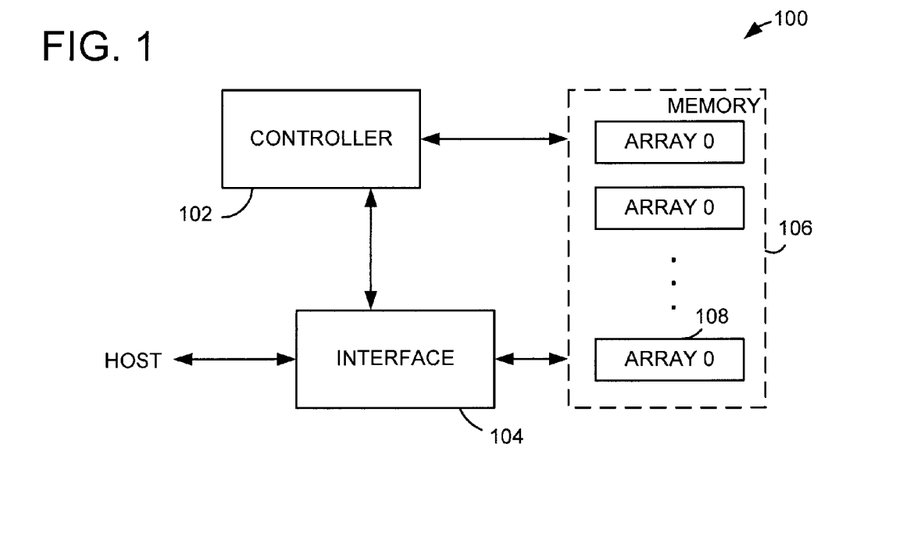
FIG. 1 is a generalized functional representation of an exemplary data storage device constructed and operated in accordance with various embodiments of the present invention.

FIG. 1 provides a functional block representation of a data storage device 100 constructed and operated in accordance with various embodiments of the present invention. Top level control of the device 100 is carried out by a suitable controller 102, which may be a programmable or hardware based microcontroller. The controller 102 communicates with a host device via a controller interface (I/F) circuit 104. A memory space is shown at 106 to comprise a number of memory arrays 108 (denoted Array 0-N), although it will be appreciated that a single array can be utilized as desired. Each array 108 comprises a block of semiconductor memory of selected storage capacity. Communications between the controller 102 and the memory space 106 are coordinated via the I/F 104.

It can be appreciated that the memory space 106 can be configured in various different ways with a variety of write and read circuitry. One such configuration can be a cross-point array of memory 110 shown in FIG. 2. A plurality of memory cells 112 can each be connected between a word line 114 and a bit line 116. In some embodiments, the word lines can be controlled by column drivers 118 and the bit lines can be controlled by row drivers 120.

Figure 2:
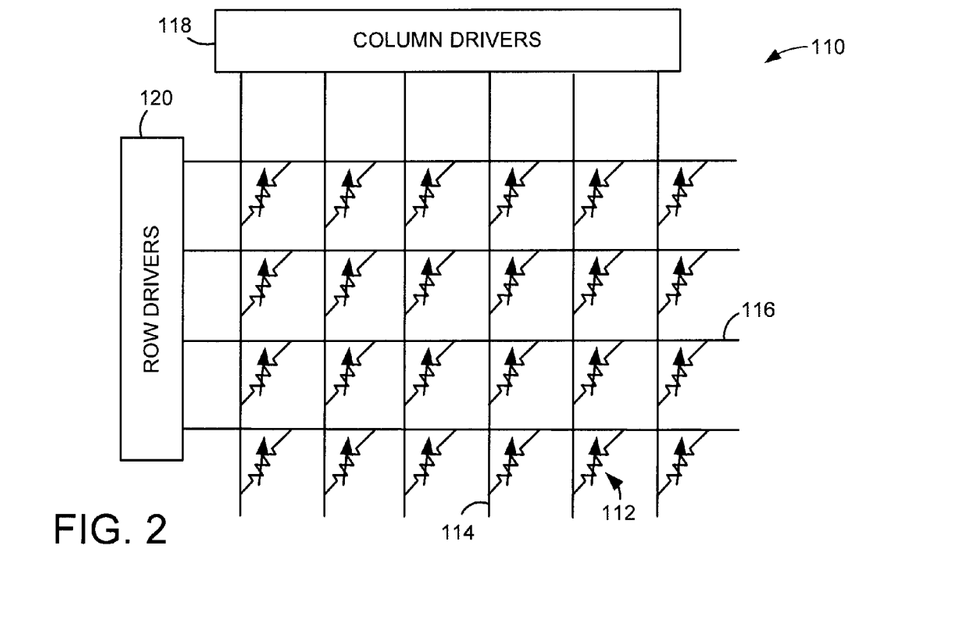
FIG. 2 shows circuitry used to read data from and write data to a memory array of the device of FIG. 1.

Further, the word lines 114 and bit lines 116 can be oriented in an orthogonal relationship to each other, but such configuration is not required or limiting. The configuration of the cross-point array 110 can be characterized as being arranged in rows and columns in which each word line 114 connects multiple memory cells along an aligned column to the column drivers 118 while each bit line 116 connects multiple memory cells along an aligned row to the row drivers 120.

However, it should be noted that the orientation of bit lines 174 and word lines 176 shown in FIG. 2 is purely exemplary and in no way limiting to the possible configurations of the cross-point array of memory cells 110. That is, a bit line 116 can connect memory cells along a column while a word line 114 connects memory cells along a row. Likewise, the number, size, and orientation of the various line drivers 118 and 120 are not limited and can be modified from the displayed configuration, as desired. For example, line drivers either alone or in combination can be used to configure the bit and word lines 116 and 114 to direct current through a one, or many, memory cells at a time.

In various embodiments of the present invention, each memory cell 112 of the cross-point array of memory can be configured with a non-ohmic switching device. Such a switching device can provide increased reliability that memory cells are not being inadvertently accessed. The addition of a switching device to the memory device can be configured in a variety of ways such as, but not limited to, a transistor connected in series with a resistive sense element (RSE) at each crossing point of the word line 114 and bit line 116.

As can be appreciated, the addition of a switching device to each memory cell can be controlled by a separate control line. As such, the control line can be configured to provide a signal to activate the switching device and allow current to flow through a selected memory cell by a selection driver. However, in various embodiments a switching device can be connected to the bit line 116 or word line 114 to effectively eliminate the need for a selection driver. Regardless, the incorporation of a switching device can provide additional selection capabilities for a cross-point array of memory cells 110 that can allow increased precision for data access.

Figure 3:
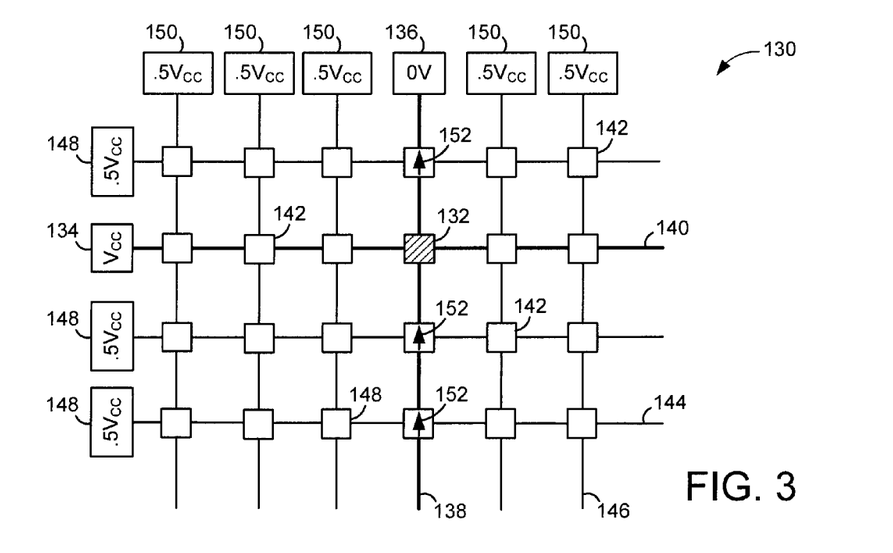
FIG. 3 displays an exemplary cross-point array of memory cells.

FIG. 3 generally illustrates an exemplary operation of a cross-point array of memory 130. In operation, current flowing through a selected memory cell 132 produces a voltage that can indicate a corresponding resistive state. Such resistive state can then be sensed to determine a logical state for the selected memory cell 132. A bit line driver 134 and a word line driver 136 corresponding to the bit line 138 and word line 140 connected to the selected memory cell 132 can be configured to different read voltages, as shown, to allow current to pass from one line driver through the memory cell 132 to the other line driver to measure a voltage. It can be appreciated that such current path is merely exemplary as the current can flow from word line 140 to bit line 138.

Further in an exemplary operation, the remaining non-selected memory cells 142 can be precharged with a predetermined voltage, such as 0.5Vcc, to avoid producing noise in the non-selected bit lines 144 and word lines 146. As illustrated in FIG. 3, a non-selected row line drivers 148 and bit line drivers 150 can be used to precharge the non-selected memory cells 142.

However, operation of a cross-point array of memory cells 130 can have disadvantages, such as the presence of unwanted leak current 152 during read operations. For example, unwanted leak current 152 can be produced from the selected word line 138 due to the potential difference between the precharged non-selected memory cells 142 and the read voltage created by the word line driver 136. As such, the higher number of memory cells connected to the selected word line 138 can result in an increased probability of error when reading the predetermined memory cell 132.

Accordingly, unwanted leak current 152 can be controlled and reduced during a read operation by including a selection circuit to the cross-point array 130 to allow current access to a predetermined number of memory cells along a column and block of memory cells while restricting access to the remaining memory cells in other blocks along the column. The addition of a block selection element that is connected between a global control line and a global selection line for each column and block of memory cells can provide such advantageous memory cell selection. That is, programming a block selection element corresponding to a selected block of memory cells to a first resistive state can allow current access to a selected memory cell in the block. Meanwhile, current can be restricted from accessing memory cells along the selected column in other blocks by programming the block selection elements corresponding to the other blocks to a second resistive state.

Figure 4:
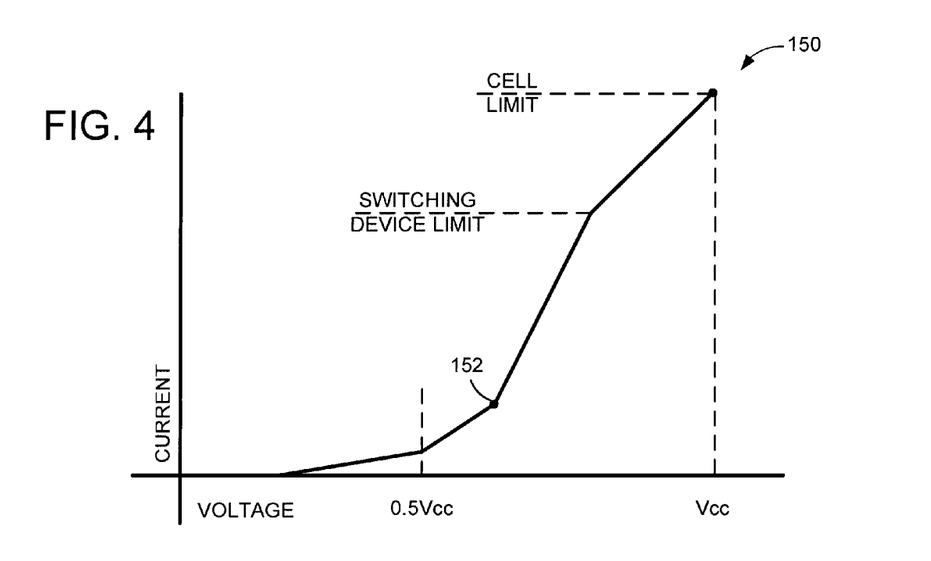
FIG. 4 graphs exemplary characteristics of the cross-point array of FIG. 3.

FIG. 4 provides a graphical illustration 150 of the characteristics of a memory cell operated in the cross-point array of memory cells shown in FIG. 3. In operation, a memory cell configured with a non-ohmic switching device provides increased selectivity by restricting current from passing through the memory cell unless a predetermined amount of voltage is present. As displayed in FIG. 3, a precharge voltage less than the switching device's limit can produce unwanted leak current 152. The presence of the unwanted leak current corresponds to point 152 in FIG. 4 as non-selected memory cells are inadvertently reaching the switching device's limit. Such events can cause the activation of the switching device and the production of read voltages for non-selected memory cells.

Figure 5:
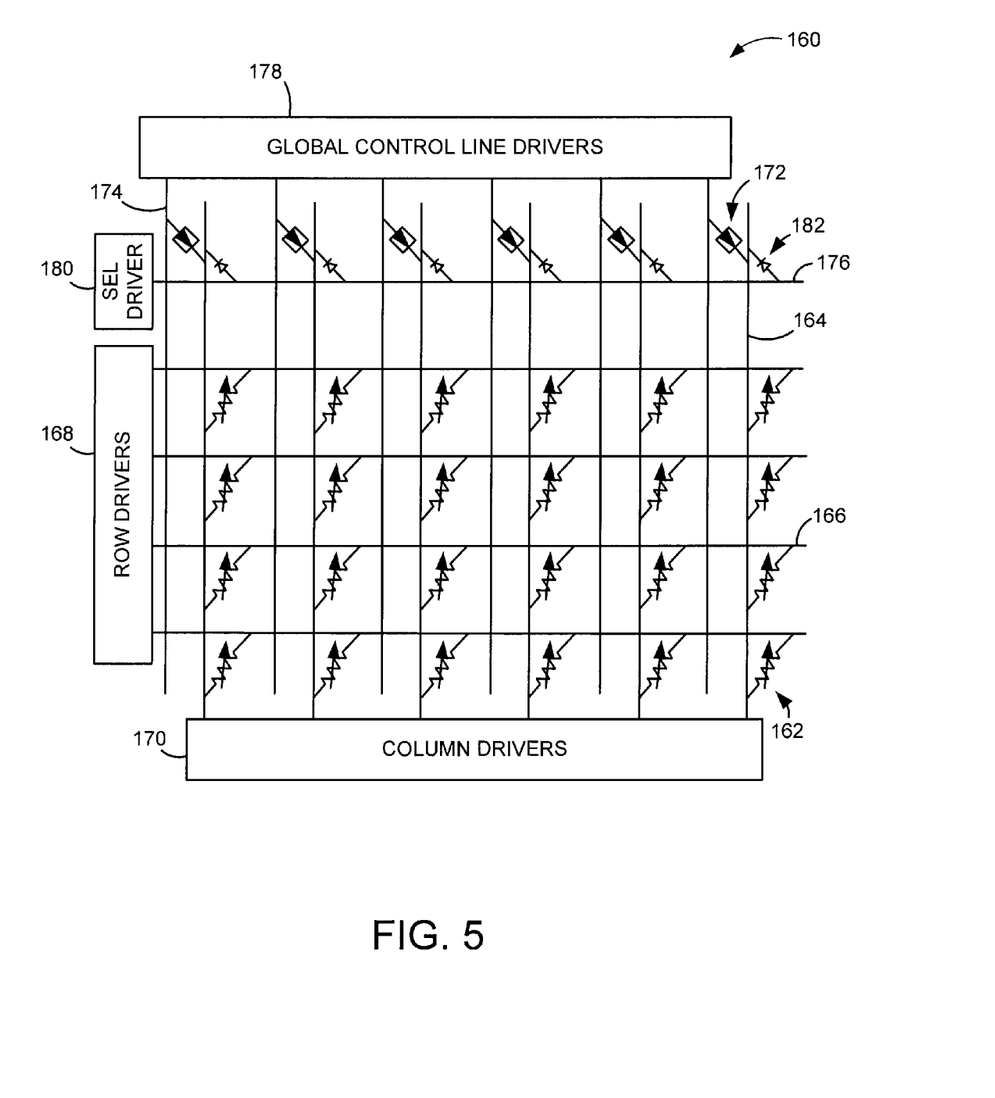
FIG. 5 displays an exemplary block of memory cells constructed and operated in accordance with various embodiments of the present invention.

In FIG. 5, an exemplary block of memory cells 160 is shown as constructed in accordance with various embodiments of the present invention. A plurality of memory cells 162 are connected to word lines 164 and bit lines 166 at the cross-point of the arranged rows and columns. In various embodiments, the bit lines 166 are controlled by one, or many row drivers 168 while the word lines 164 are controlled by one, or many, column drivers 170. The presence of unwanted leak current can be reduced in the block of memory cells 160 with the addition of a selection circuit that includes at least a block selection element 172 connected between a global control line 174 and a global selection line 176.

Control of the global control line 174 may be facilitated by at least one global control line drivers 178 while the global selection line 176 is controlled by at least one selection driver 180. The global control line and selection drivers 178 and 180 can be configured to program a first or second resistive state to one, or all, the block selection elements 172 by passing a program current through the desired element(s) 172. As a result, current passing through the memory cells 162 of the block 160 can be manipulated so that only a desired word line 164 receives current. For example, a high resistive state can be programmed to the block selection elements 172 of non-selected word lines 164 through signals sent exclusively through the global control lines 174 and the global selection line 176 to prevent current from passing through the memory cells 162 connected to the word lines 164 corresponding to the programmed block selection elements 172.

In contrast, the programming of a block selection element 172 to a low resistive state can allow current to pass through the word line 164 connected to the programmed block selection element 172. During the reading of a logical state from a memory cell 162, a current can possibly pass through the global selection line 176. Some embodiments of the present invention prevent such flow of current with the connection of a uni-flow device 182 between each word line 164 and the global selection line 176. As displayed, a plurality of uni-flow devices 182 can be oriented in opposing directions and connected in series to each word line 164. It can be appreciated that such uni-flow device orientation can be characterized in various embodiments as a magic diode.

It should be noted that while each memory cell 162 in the array of memory cells 160 is shown with only an RSE, such configuration is not limiting as a switching device can be connected in series with one, or many, of the RSE, as desired. Similarly, the orientation of the block selection elements 172 and uni-flow devices 182 is not restricted to the configuration shown in FIG. 5. For example, a separate second global selection line (not shown) can be connected to each word line 164 with a uni-flow device while the block selection element 172 is connected in series with a uni-flow device 182 to the original global selection line 172.

Figure 6:
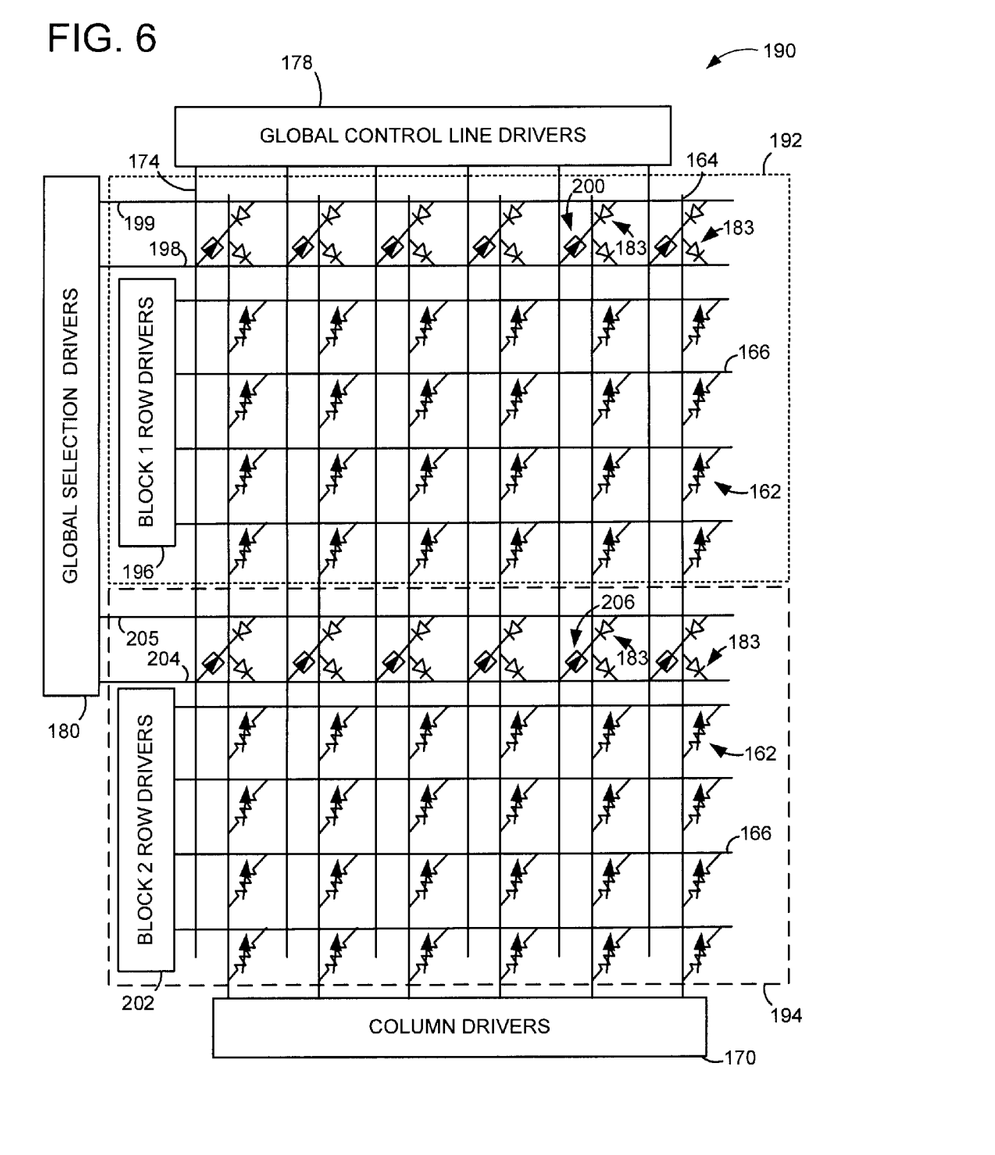
FIG. 6 illustrates an exemplary array of memory cells constructed and operated in accordance with various embodiments of the present invention.

FIG. 6 generally illustrates an array of memory cells 190 constructed in accordance with various embodiments of the present invention. A first and second block of memory cells 192 and 194, such as the block of memory cells 160 of FIG. 5, can be connected by common word lines 164 and global control lines 174 to construct the array 190. However, the displayed configuration is not limiting as blocks of memory cells can be connected in a variety of ways while keeping with the spirit of the present invention.

The selection of the memory cells connected to the bit lines 166 of the first block can be facilitated by the combination of block 1 row drivers 196, first block 1 global selection control line 198, second block 1 global selection control line 199, and the programmed state of the block 1 selection elements 200. Consequently, memory cells of a particular word line 164, but only in the first block 192, can be accessed with a particular programming configuration of the resistive states of the block selection elements 200 corresponding to the first block of memory cells 192.

In various embodiments, such programming configuration has a plurality of uni-flow devices 183 connected between a word line 164 and either of the first or second block 1 global selection control lines 198 or 199 and oriented in opposing directions. This configuration can allow for the first and second block 1 global selection lines 198 and 199 to be activated once per access to block 1 while preventing current from inadvertently passing to the memory cells 162. In contrast, the combination of the block 2 row drivers 202, first block 2 global selection control line 204, second block 2 global selection control line 205, and one, or many, of the block 2 selection elements 206 corresponding to the second block 194 can provide access to only predetermined second block memory cells while excluding current from passing through the first block memory cells.

As shown, the array of memory cells 190 can be configured to allow access to a predetermined number of memory cells 162 while restricting access to other memory cells 162. However, the possible configurations of the various block selection elements 198 and 202 are not limited. For example, a memory cells from both the first and second blocks 192 and 194 can be accessed simultaneously or consecutively with the configuration of the corresponding block 1 and block 2 selection elements 200 and 206 by the respective block 1 and block 2 global selection control lines 198 and 204 in combination with the global control line drivers 178.

Furthermore, the size of the array 190 shown in FIG. 6 does not restrict or limit the numerous configurations of rows, columns, and blocks of memory cells. That is, each block of memory can be oriented with any number of word lines, bit lines, memory cells, and global control lines. Likewise, the number of blocks of memory cells can vary, as desired, to create an array of memory cells. For example, ten blocks of memory cells can be connected via common global control lines and word lines can be created just as two blocks of memory cells can have ten global control lines.

In sum, the orientation of the array of memory cells 190 can vary greatly, but the selection circuitry at least comprises a number of block selection elements equal to the number of overall blocks of memory cells and columns as well as a number of global selection control lines equal to the number of blocks of memory. An example of the operation of such an alternative array of memory cells can be found in FIG. 7.

Figure 7:
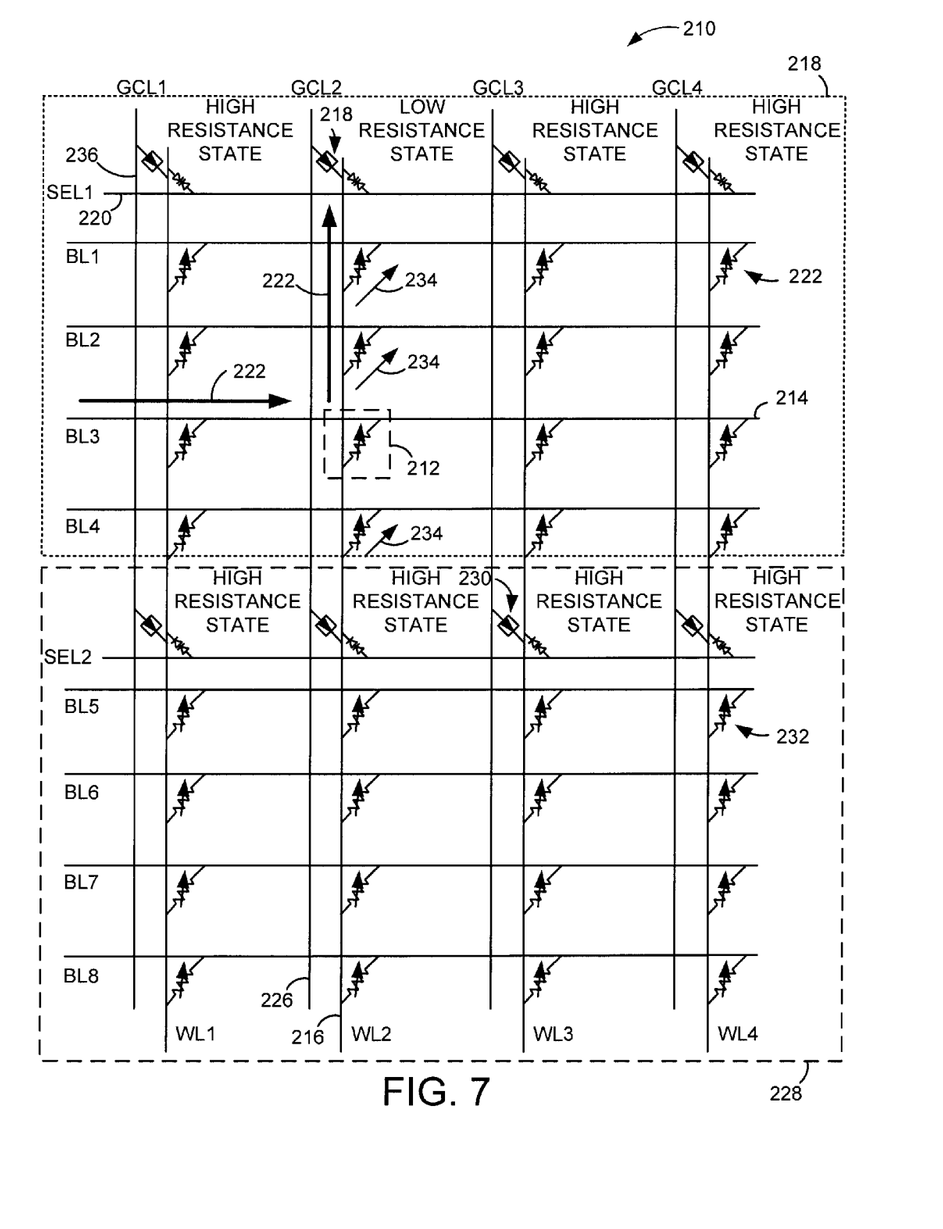
FIG. 7 provides an exemplary operation of the array of memory cells of FIGS. 5 and 6 performed in accordance with various embodiments of the present invention.

An exemplary operation of an array of memory cells 210 is provided in FIG. 7 in accordance with various embodiments of the present invention. A selection of a particular memory cell 212 to read corresponds, in some embodiments, with a selected bit line 214, word line 216, block 218, global block 1 selection control line 220, global control line 222, and block 1 selection element 224. A read current 226 can pass through the selected memory cell 212 once the block 1 selection element 224 connected to the global control line 222 connected to the word line 216 is programmed to a low resistive state. Such programming can be facilitated by passing a program current from the global block 1 selection control line 220 through the block 1 selection element 224 to the global control line 222, or vice versa.

Further in various embodiments, in combination with the programming of the selected block 1 selection element 224, the non-selected block 1 and block 2 selection elements 228 are to be programmed to a high resistive state. The programming of the non-selected selection elements 230 can be accomplished in a variety of times. That is, the programming of all the non-selected selection elements 230 can be performed successively or simultaneously with the global selection control lines to prevent unwanted leak current from being induced in the non-selected memory cells 232. Regardless, as the read current 226 passes through the selected memory cell 212, unwanted leak current 232 is greatly reduced when the non-selected selection elements 230 are programmed to a high resistive state before the read current 226 is generated.

However, it can be appreciated that a residual amount of unwanted leak current 234 can be present and affect the read current 226 due to the connection of multiple memory cells along the word line 216 configured to allow current to pass, as shown in FIG. 3. While a residual amount of leak current may be present in the read current 226, the very low number of memory cells leaking current will likely not practically affect the efficiency or reliability of reading the selected memory cell 212.

It should be noted that the read operation depicted in FIG. 7 is merely exemplary and can be modified in scope, duration, and frequency. As such, the array of memory cells 210 can readily and quickly be reconfigured to pass a read current through one, or many, memory cells. Such efficiency can be aided by the connection of all the block selection elements along a block of memory to a single global selection control line. Hence, all the block selection elements can be programmed to a common resistive state with the activation of the global selection control lines and the global control lines concurrently, or in succession.

Figure 8:
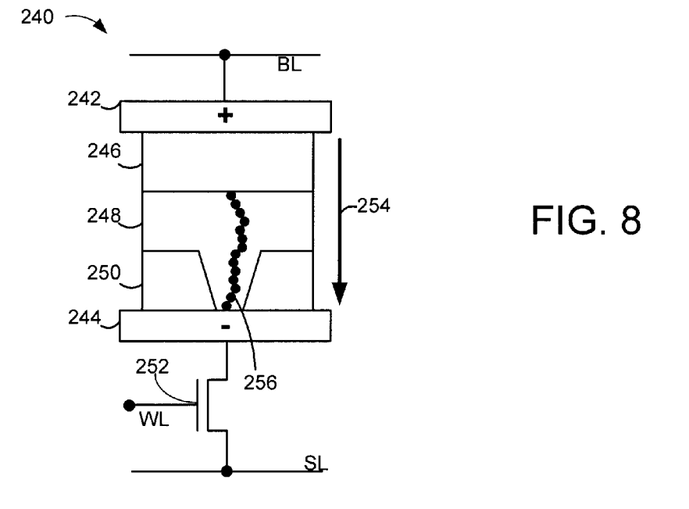
FIG. 8 illustrates an exemplary block selection element capable of being used in the memory array of FIGS. 5-7.
Figure 9:
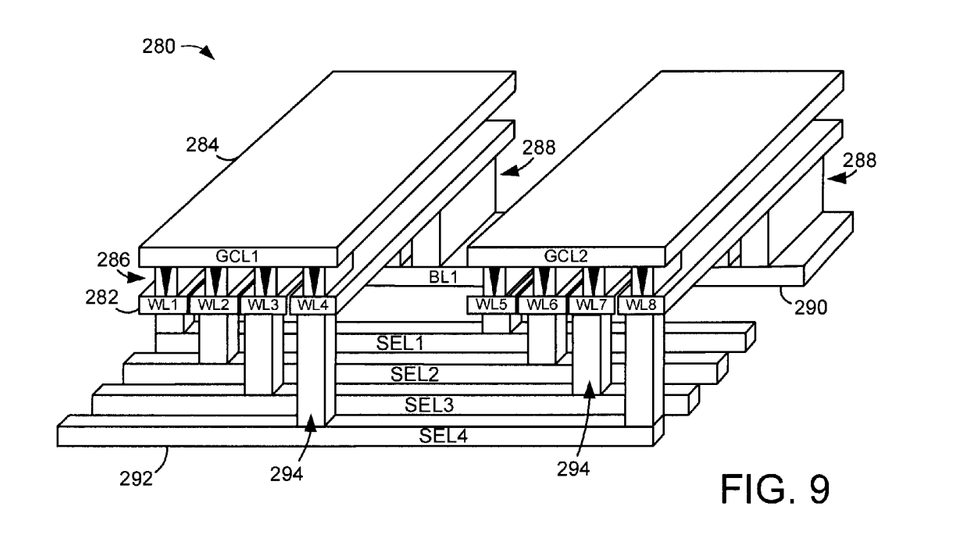
FIG. 9 displays an exemplary array of memory cells constructed and operated in accordance with various embodiments of the present invention.

In FIG. 8, an exemplary block selection element 240 constructed as a programmable metallization cell (PMC) is shown as constructed in accordance with various embodiments of the present invention. A first electrode 242 and a second electrode 244 bound a metal layer 246, an embedded layer 248, and a dielectric layer 250. The relative potential between the first and second electrodes 242 and 244 can be adjusted with a switching device 252 to allow a write current 254 to pass through the PMC 240 and form a filament 256.

With a forward bias through the PMC 240, the filament 256 forms a connection between the metal layer 246 and the second electrode 244 in the embedded layer 248 by the migration of ions from the metal layer 246 and electrons from the second electrode 244. Further, a dielectric layer 250 focuses a small area of possible electron migration from the second electrode 244 to the embedded layer 248 in order to contain the position of the formed filament 256. The resultant resistive relationship of the embedded layer 248 to the metal layer 246 defines the logical state of the PMC 240 through the existence of a high or low resistive state depending on the existence of a formed filament 256.

In operation, a reverse bias direction of the current pulse 254 that causes a dissipation of the previously formed filament 256. The dissipation is facilitated through reversing the polarization of the electrodes and causing the ions to migrate towards the electrodes 244 and 246. The use of currents with either positive or negative polarity to set different resistance state displays the bipolar nature of a PMC 240.

In some embodiments, the PMC 240 is constructed in reverse sequence so that the filament forming current pulse and filament dissipating pulse are the reverse of the pulses shown in FIG. 8. Further in some embodiments, the direction of the current pulse 254 can oppose the migration direction of the metal ions that form the filament 256.

Further in some embodiments, the embedded layer 248 is constructed of a thin film composite of Praseodymium, Calcium, Manganese, and Oxygen PrCaMnO (PCMO). The application and function of a PCMO in a PMC 240 does not substantially change the ability to store resistive states or be configured as a switching device with bipolar characteristics.

It should be noted that the various memory cells depicted throughout the figures are not limited to a particular type or construction. For example, a memory cell, such as memory cell 162 of FIG. 5, can be configured as a resistive random access memory (RRAM) cell that includes a resistive storage layer that is disposed between a first electrode layer and a second electrode layer. An RRAM cell has a naturally high resistive value due to the composition and properties of the storage layer, which can be an oxide (such as magnesium oxide, MgO) with normally high electrical resistance.

However, a low resistive value is created when a predetermined pulse is applied so that a predetermined amount of current passes through the storage layer and one or more filaments are formed therein. The formed filament functions to electrically interconnect the first electrode layer and the second electrode layer. The filament formation process will generally depend on the respective compositions of the layers, but generally, a filament such as can be formed through the controlled metal migration (e.g., Ag, etc.) from a selected electrode layer into the oxide storage layer.

The subsequent application of a voltage pulse of increased current across them memory cell will generally drive the metal from the storage layer back into the associated electrode layers, removing the filament from the storage layer and returning the memory cell 260 to the initial high resistance state. Such application of voltage can be facilitated, in some embodiments, by the selection of a switching device.

Another possible configuration of a memory cell can be as a spin-torque transfer random access memory (STRAM). In such a memory cell, a fixed reference layer and a programmable free layer (recording layer) are separated by an intervening tunneling (barrier) layer. The reference layer has a fixed magnetic orientation in a selected direction, as indicated by arrow. The free layer has a selectively programmable magnetic orientation that can be parallel or anti-parallel with the selected direction of the reference layer.

A low resistance state for the STRAM cell can be achieved when the magnetization of the free layer is oriented to be substantially in the same direction (parallel) as the magnetization of the reference layer. To orient the cell in the parallel low resistance state, a write current passes through the cell so that the magnetization direction of the reference layer sets the magnetic orientation of the free layer. Since electrons flow in the direction opposite to the direction of current, the write current direction passes from the free layer to the reference layer, and the electrons travel from the reference layer to the free layer.

In contrast, a high resistance state for the cell can established in the anti-parallel orientation in which the magnetization direction of the free layer is substantially opposite that of the reference layer. To orient the cell in the anti-parallel resistance state, a write current passes through the cell from the reference layer to the free layer so that spin-polarized electrons flow into the free layer in the opposite direction.

Figure 10:
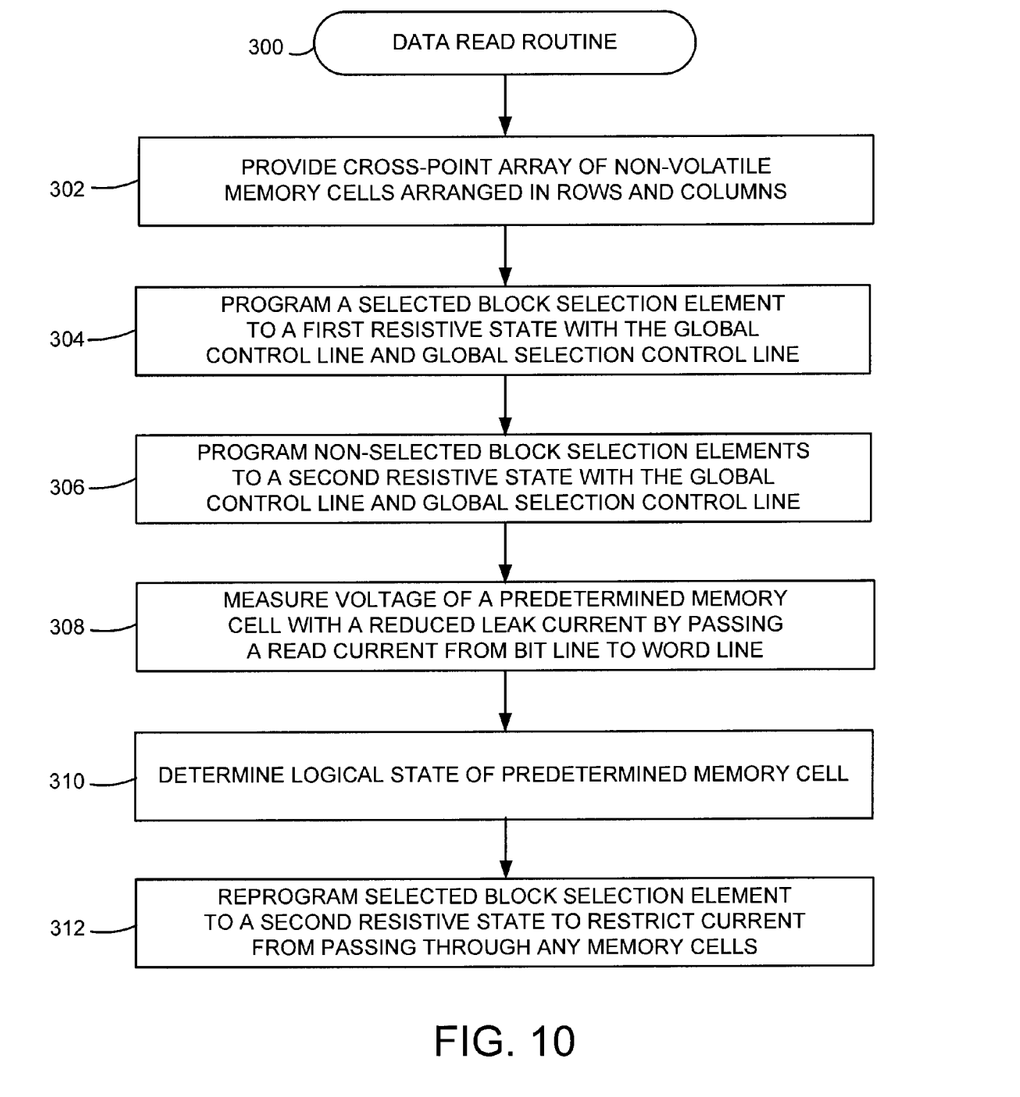
FIG. 10 provides a flowchart of a page read routine performed in accordance with various embodiments of the present invention.

An alternative embodiment an array of memory cell 280 is shown in FIG. 10. A plurality of word lines 282 can be connected to a single global control line 284. As shown, each global control line 284 can be connected to multiple word lines 282 through a block selection element 286. Further, the each word line 282 can be connected to a memory cell 288 and a bit line 290, respectively. The selection of a predetermined one, or many, of the block selection elements 286 can be facilitated with one or more of the global selection control line 292 and the uni-flow device 294 connected to each word line 282. As a result, the number of global control lines present in the array of memory cells 280 can be reduced while providing advantageous selection and restriction of current through predetermined memory cells.

However, it should be noted that the number and orientation of the uni-flow devices 294 and global selection control lines 292 can vary, as displayed. For example, the first global selection control line (SEL1) can be set to a low voltage while the first global control line (GCL1) 284 is set to a high voltage to connect the GCL1 to the first word line (WL1) 282. Conversely, setting SEL1 to a low voltage and GCL2 to a high voltage may result in GCL2 connecting to the fifth word line (WL5). In other embodiments of the present invention, the global selection control lines 292 can be coupled to a plurality of uni-flow devices 294 connecting the global control lines 284 to the word lines 282.

FIG. 11 provides a flowchart of a data read routine 300 performed in accordance with various embodiments of the present invention. The data read routine 300 initially provides a cross-point array of memory cells arranged into columns and rows in step 302. Subsequently in step 304, a selected block selection element corresponding to a predetermined memory cell is programmed to a first resistive state with the global control lines and global selection control lines. The remaining non-selected block selection elements corresponding to non-selected memory cells are programmed to a second resistive state with the global control lines and global selection control lines at step 306. It should be noted that the timing of steps 304 and 306 is not limited and the steps can be performed in any order either concurrently or successively.

Furthermore in step 308, a voltage a measured from the predetermined memory cell with a read current that can include an amount of leak current generated by non-selected memory cells along the selected word line. The measured voltage is subsequently evaluated to determine a logical state of the predetermined memory cell at step 310. Finally, the selected block selection element is reprogrammed to the second resistive state to restrict current from passing through any memory cells at step 312.

As can be appreciated by one skilled in the art, the various embodiments illustrated herein provide advantageous reading of data from a memory cell in an efficient manner. The use of block selection elements to allow current to pass through only a predetermined number of memory cells along a column allows for a reduction in unwanted leak current that leads to increased reliability of memory array operation. With several global control lines, access to particular rows, columns, and blocks of memory cells can be efficiently manipulated to provide functional bandwidth and data throughput. However, it will be appreciated that the various embodiments discussed herein have numerous potential applications and are not limited to a certain field of electronic media or type of data storage devices.

It is to be understood that even though numerous characteristics and advantages of various embodiments of the present invention have been set forth in the foregoing description, together with details of the structure and function of various embodiments of the invention, this detailed description is illustrative only, and changes may be made in detail, especially in matters of structure and arrangements of parts within the principles of the present invention to the full extent indicated by the broad general meaning of the terms in which the appended claims are expressed.

What is claimed is:

1. A memory device comprising:
   a cross-point array of non-volatile memory cells arranged into rows and columns; and
   a read circuit capable of reading a logical state of a predetermined memory cell in the first block of memory cells with a reduced leak current by programming a first resistive state to the at least one first resistive random access memory (RRAM) block selection element while programming a second resistive state to at least one second RRAM block selection element, the block selection element respectively connected at least two global selection control lines with a uni-flow device.

2. The memory device of claim 1, wherein a plurality of rows define the first block of memory cells and the second block of memory cells.

3. The memory device of claim 1, wherein the first and second blocks of memory cells are connected in series along each column.

4. The memory device of claim 1, further comprising a selection circuit with a selection block selection element connected between a global control line and a global selection control line for each block and column.

5. The memory device of claim 4, wherein the selection circuit is capable of activating a first block of memory cells while deactivating a second block of memory cells.

6. The memory device of claim 4, wherein each global control line is connected to only the number of selection block selection elements equal to the number of blocks of memory cells.

7. The memory device of claim 4, wherein the selection block selection element is characterized as a programmable metallization cell (PMC).

8. The memory device of claim 4, wherein the selection block selection element is connected in series with a diode.

9. The memory device of claim 1, wherein the first and second RRAM block selection elements are each resistive random access memory (RRAM) cells.

10. The memory device of claim 7, wherein the RSE is characterized as resistive random access memory (RRAM) cells.

11. The memory device of claim 1, further comprising a uni-flow device that prevents current below a predetermined threshold from passing through the RRAM block selection element.

12. A method comprising the steps of providing a cross-point array of non-volatile memory cells arranged into rows and columns and a read circuit, and reading a logical state of a predetermined memo in the first block of memory cells with a reduced leak current by programming a first resistive state to at least one first resistive random access memory (RRAM) block selection element while programming a second resistive state to at least one second RRAM block selection element, the block selection element respectively connected to first and second global selection control lines with a uni-flow device.

13. The method of claim 12, further comprising a selection circuit with a selection block selection element connected between a global control line and a global selection control line for each block and column.

14. The method of claim 13, wherein each global control line is connected to only the number of selection block selection elements equal to the number of blocks of memory cells.

15. The method of claim 13, wherein a single global selection control line programs the resistive state of all the selection block selection elements of a selected block of memory cells.

16. The method of claim 13, wherein the selection block selection element is characterized as a resistive random access memory (RRAM) cell.

17. The method of claim 13, wherein the selection block selection element is programmed by passing a current through the global control line and the global selection control line.

18. The method of claim 12, wherein a resistive sense element (RSE) is connected between a row and column.

19. The method of claim 12, wherein an amount of leak current is measured while reading the predetermined memory cell.

20. An apparatus comprising:
   a cross-point array of non-volatile memory cells arranged into rows and columns; and
   a read circuit capable of reading a logical state or a predetermined memory cell in the first block of memory cells with a reduced leak current by programming a first resistive state to the at least one first resistive random access memory (RRAM) block selection element while programming a second resistive state to at least one second block selection element, wherein a first global control line manages each of the first RRAM block selection elements and a second global control line manages each of the second block selection elements, and wherein each first RRAM and the second selection element resides in a common horizontal plane between the non-volatile memory cells and the global control lines, the block selection element respectively connected to first and second global selection control lines with uni-flow devices oriented in opposing directions.

21. The memory device of claim 1, wherein at least one non-volatile memory cell has a resistive sense element connected in series with a non-ohmic device.

* * * * *